United States Patent
Haese et al.

(10) Patent No.: US 7,550,632 B2
(45) Date of Patent: Jun. 23, 2009

(54) METHODS OF TREATING TRIETHANOLAMINE WITH ACID COMPONENTS AND BASIC COMPONENTS, AND TRIETHANOLAMINE COMPOSITIONS CONTAINING THE SAME

(75) Inventors: Frank Haese, Bollingstedt (DE); Johann-Peter Melder, Böhl-Iggelheim (DE); Roman Dostalek, Neuleiningen (DE); Manfred Julius, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 143 days.

(21) Appl. No.: 11/661,544

(22) PCT Filed: Aug. 4, 2005

(86) PCT No.: PCT/EP2005/008441

§ 371 (c)(1),
(2), (4) Date: Feb. 27, 2007

(87) PCT Pub. No.: WO2006/024358

PCT Pub. Date: Mar. 9, 2006

(65) Prior Publication Data

US 2007/0276161 A1 Nov. 29, 2007
US 2009/0131722 A9 May 21, 2009

(30) Foreign Application Priority Data

Aug. 31, 2004 (DE) .................. 10 2004 042 453

(51) Int. Cl.
C07C 209/84 (2006.01)

(52) U.S. Cl. .................................................. 564/497

(58) Field of Classification Search ................ None
See application file for complete search history.

(56) References Cited

U.S. PATENT DOCUMENTS

| | | | |
|---|---|---|---|
| 3,207,790 A | 9/1965 | Glew et al. | |
| 3,387,934 A | 6/1968 | Minkiei | |
| 4,567,303 A | 1/1986 | Boettger et al. | |
| 5,545,757 A | 8/1996 | Hammer et al. | |
| 5,693,866 A | 12/1997 | Roling et al. | |
| 6,291,715 B1 | 9/2001 | Ruider et al. | |
| 6,323,371 B2 | 11/2001 | Ruider et al. | |
| 6,388,137 B1 | 5/2002 | Ruider et al. | |

FOREIGN PATENT DOCUMENTS

| | | |
|---|---|---|
| EP | 0 004 015 | 9/1979 |
| EP | 4 015 | 9/1979 |
| EP | 0 036 152 | 9/1981 |
| EP | 36 152 | 9/1981 |
| EP | 673 920 | 9/1995 |
| EP | 1 081 130 | 3/2001 |
| EP | 1 081 136 | 3/2001 |
| EP | 1 132 371 | 9/2001 |
| WO | WO 00/32553 | 6/2000 |
| WO | WO-00/32553 | 6/2000 |

OTHER PUBLICATIONS

Mosher, E. et al., "The Chemical Control of Phosphine Gas Generation During the Machining of Nodular Cast Iron", Lubrication Engineering 45(7) (1989), pp. 445-450.

*Primary Examiner*—Brian J Davis
(74) *Attorney, Agent, or Firm*—Connolly Bove Lodge & Hutz LLP

(57) ABSTRACT

Methods for improving color properties of triethanolamine, and triethanolamine compositions treated thereby, are disclosed, wherein the methods comprise: (a) providing a composition comprising triethanolamine; and (b) contacting the composition with an acid component and a basic component; wherein the acid component comprises an acid selected from the group consisting of phosphorous acid, hypophosphorous acid and mixtures thereof; and wherein the basic component comprises a compound selected from the group consisting of alkali metal hydroxides, alkaline earth metal hydroxides, ammonium hydroxides according to general formula (I), and mixtures thereof:

$$[R^1R^2R^3(2\text{-hydroxyethyl})\text{ammonium}] \text{ hydroxide} \quad (I)$$

wherein $R^1$, $R^2$ and $R^3$ each independently represents a $C_{1-30}$ alkyl or a $C_{2-10}$ hydroxyalkyl; with the proviso that where the basic component comprises an alkali metal hydroxide, the molar ratio of acid component: basic component is 1:0.1 to 1:1, and where the basic component comprises an alkaline earth metal hydroxide, the molar ratio of acid component: basic component is 1:0.05 to 1:0.5.

20 Claims, No Drawings

METHODS OF TREATING TRIETHANOLAMINE WITH ACID COMPONENTS AND BASIC COMPONENTS, AND TRIETHANOLAMINE COMPOSITIONS CONTAINING THE SAME

CROSS-REFERENCE TO RELATED APPLICATIONS

This application is a national stage application, under 35 U.S.C. §371, of PCT/EP2005/008441 filed Aug. 4, 2005, which claims benefit of German Application No. 10 2004 042 453.5 filed Aug. 31, 2004.

BACKGROUND OF THE INVENTION

Important fields of use of triethanolamine (TEOA) or its secondary products are, for example, soaps, detergents and shampoos in the cosmetics industry and also dispersants and emulsifiers.

For these and other fields of use, water-clear, colorless triethanolamine with the slightest possible discoloration, e.g. measured as APHA or Gardner color number, which retains these properties even over prolonged storage periods (of e.g. 6, 12 or more months) is desired.

A known problem is that a pure TEOA obtained by fractional distillation of a triethanolamine crude product which has been obtained, for example, by reacting ammonia with ethylene oxide has a yellowish to brownish or pink discoloration (color number e.g. about 10 to 500 APHA in accordance with DIN ISO 6271 (=Hazen)). This discoloration arises particularly in processes in which high temperatures are passed through.

During storage of the alkanolamine, even in a sealed pack and with the exclusion of light, this discoloration is further intensified. (See e.g.: T. I. MacMillan, Ethylene Oxide Derivatives, report No. 193, chapter 6, pages 6-5 and 6-9 to 6-13, 1991, SRI International, Menlo Park, Calif. 94025;

G. G. Smirnova et al., J. of Applied Chemistry of the USSR 61, pp. 1508-9 (1988), and Chemical & Engineering News 1996, Sep. 16, page 42, middle column).

The literature describes various methods of producing triethanolamine with improved color quality.

EP-A-36 152 and EP-A-4015 (both BASF AG) explain the influence of the materials used in methods of producing alkanolamines on the color quality of the process product and recommend nickel-free and/or low-nickel steels.

U.S. Pat. No. 3,207,790 (Dow Chemical Company) describes a method of improving the color quality of alkanolamines by adding a boron hydride of an alkali metal.

EP-A-1 081 130 (BASF AG) relates to a method of producing alkanolamines with improved color quality by treating the alkanolamine with hydrogen in the presence of a hydrogenation catalyst.

EP-A-4015 (BASF AG) describes that mono-, di- and triethanolamine with less discoloration are obtained by adding phosphorous or hypophosphorous acid or derivatives thereof before or during or directly after the stepwise reaction of ethylene oxide with ammonia and subsequent isolation by distillation.

WO-A-00/32553 (BASF AG) relates to a method of purifying TEOA produced by the reaction of aqueous ammonia with ethylene oxide in liquid phase under pressure and at elevated temperature by separating off excess ammonia, water and monoethanolamine from the reaction product, reacting the crude product obtained in this way with ethylene oxide and then rectifying it in the presence of phosphorous or hypophosphorous acid or compounds thereof.

EP-A-1 132 371 (BASF AG) relates to a method of producing alkanolamines with improved color quality where the alkanolamine is treated with an effective amount of phosphorous or hypophosphorous acid or compounds thereof firstly at elevated temperature over a period of at least 5 min (step a) and is then distilled in the presence of an effective amount of one of these phosphorous compounds (step b).

BRIEF SUMMARY OF THE INVENTION

The present invention relates to a method of producing triethanolamine and triethanolamine comprising phosphorous and/or hypophosphorous acid and certain basic compounds.

The object of the present invention was to provide a method of producing triethanolamine with good color quality which is improved compared with the prior art. The method is intended to reduce the discoloration of TEOA, e.g. measured as APHA color number, and improve the color stability (undesired increase in the color number over the storage period). In particular, the method was to produce higher yields of TEOA compared with EP-A-4015, WO-A-00/32553 and EP-A-1 132 371.

Accordingly, a method of producing triethanolamine has been found wherein phosphorous and/or hypophosphorous acid and a basic compound chosen from alkali metal hydroxide, alkaline earth metal hydroxide and [$R^1R^2R^3$(2-hydroxyethyl)-ammonium] hydroxide, where $R^1$, $R^2$ and $R^3$, independently of one another, are $C_{1-30}$alkyl or $C_{2-10}$-hydroxyalkyl, are added to the triethanolamine and in the case of alkali metal hydroxide as basic compound the molar ratio of acid(s):hydroxide is in the range from 1:0.1 to 1:1 and in the case of alkaline earth metal hydroxide as basic compound the molar ratio of acid(s):hydroxide is in the range from 1:0.05 to 1:0.5.

In addition triethanolamine comprising phosphorous and/or hypophosphorous acid and $R^1R^2R^3$(2-hydroxyethyl)ammonium] hydroxide, where $R^1$, $R^2$ and $R^3$, independently of one another, are $C_{1-30}$-alkyl or $C_{2-10}$-hydroxyalkyl, has been found.

In addition, triethanolamine comprising phosphorous and/or hypophosphorous acid and an alkali metal hydroxide or alkaline earth metal hydroxide, where in the case of alkali metal hydroxide the molar ratio of acid(s):hydroxide is in the range from 1:0.1 to 1:1 and in the case of alkaline earth metal hydroxide the molar ratio of acid(s):hydroxide is in the range from 1:0.05 to 1:0.5, has been found.

Preferred molar ratios of acid(s):hydroxide in the triethanolamine are given in the description below.

According to the invention, it has been recognized that while retaining or even improving the color quality compared with the sole use of $H_3PO_3$ or $H_3PO_2$, the formation of by-products in the TEOA is significantly reduced as a result of the additional basic compound (buffer effect of the base). At the same time, the TEOA distillation yield is increased. The by-product formation is presumably based on the acidic effect of the phosphorous compounds.

DETAILED DESCRIPTION OF THE INVENTION

The triethanolamine used in the method according to the invention can be obtained by known methods, in particular by reacting ammonia with ethylene oxide (e.g. as in EP-A-673 920 or WO-A-00/32553).

The purity of the triethanolamine used in the method according to the invention is preferably greater than 70% by weight, in particular greater than 80% by weight. Besides distilled or undistilled crude triethanolamine, which can also be removed directly in crude form from a plant for producing alkanolamine from the corresponding precursors, it is also possible to use distilled TEOA with a purity of greater than 90% by weight, e.g. greater than 95% by weight, particularly ≧97% by weight, in particular ≧98% by weight, very particularly ≧99% by weight.

It is also possible to use mixtures of triethanolamine with other alkanolamines, such as, for example, monoethanolamine (MEA), diethanolamine (DEA), aminodiglycol (ADG, H$_2$NCH$_2$CH$_2$OCH$_2$CH$_2$OH), O,N,N-tris(2-hydroxyethyl) ethanolamine, N-(2-aminoethyl)-ethanolamine (AEEA), N-(2-hydroxyethyl)piperazine, N-(2-hydroxyethyl)morpholine, N,N'-bis(2-hydroxyethyl)piperazine, monoisopropanolamine, diisopropanolamine, triisopropanolamine and 1,3-propanolamine, or solutions of triethanolamine in an inert solvent, such as, for example, alcohols (methanol, ethanol, isopropanol, n-propanol, n-butanol, 2-ethylhexanol), ethers (tetrahydrofuran, 1,4-dioxane), hydrocarbons (benzene, pentane, petroleum ether, toluene, xylene, hexane, heptane, mihagol) and water or mixtures thereof.

The APHA color number of the triethanolamine used is preferably ≦100, in particular ≦50, very particularly ≦20.

The method according to the invention can be carried out as follows:

In a suitable container, e.g. stirred container, which may be equipped with a reflux condenser, an effective amount of phosphorous acid (H$_3$PO$_3$) and/or hypophosphorous acid (H$_3$PO$_2$) and a basic compound chosen from alkali metal hydroxide, alkaline earth metal hydroxide and [R$^1$R$^2$R$^3$(2-hydroxyethyl)ammonium] hydroxide, where R$^1$, R$^2$ and R$^3$ have the meanings given, are added to the triethanolamine whose color quality is to be improved in liquid phase, optionally in the presence of an inert solvent, advantageously with stirring or circulation pumping.

The mixture is heated over a period of preferably at least 5 min, in particular at least 10 min (for example 10 min to 50 hours, in particular 10 min to 24 hours), very particularly at least 15 min (for example 15 min to 6 hours), particularly preferably at least 30 min (for example 30 min to 4 hours or 40 min to 3 hours or 60 min to 2 hours) at a temperature in the range from 40 to 250° C., in particular 100 to 240° C., very particularly 120 to 230° C., particularly preferably 150 to 220° C.

The phosphorous acid and/or hypophosphorous acid can be used in the method according to the invention in monomeric or polymeric form, in hydrous form (hydrates or aqueous solution or aqueous suspension) or as addition compound (e.g. on an inorganic or organic support such as SiO$_2$, Al$_2$O$_3$, TiO$_2$, ZrO$_2$).

The amount of added acid(s) is generally at least 0.01% by weight, preferably 0.02 to 2% by weight, particularly preferably 0.03 to 1.0% by weight, very particularly preferably 0.5 to 0.9% by weight, based on the amount of triethanolamine used (calculated on the basis of pure substances); however, the effect also arises with relatively large amounts.

If phosphorous acid and hypophosphorous acid are used together, the above quantitative data refer to both acids together.

In the method according to the invention the basic compound which can be used is an alkali metal hydroxide, where alkali metal=Li, Na, K, Rb or Cs, preferably Na or K, an alkaline earth metal hydroxide, where alkaline earth metal=Be, Mg, Ca, Sr, Ba, or preferably an ammonium hydroxide of the formula [R$^1$R$^2$R$^3$(2-hydroxyethyl)ammonium] hydroxide, i.e.

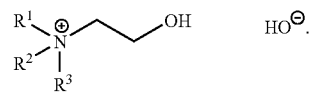

The radicals R$^1$, R$^2$ and R$^3$, independently of one another, have the following meanings:

unbranched or branched C$_{1-30}$-alkyl, among them C$_{8-22}$-alkyl, preferably C$_{1-20}$-alkyl, in particular C$_{1-14}$-alkyl, among them C$_{1-4}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-undecyl, n-dodecyl, n-tridecyl, 2-n-butyl-n-nonyl, 3-n-butyl-n-nonyl, n-tetradecyl, n-pentadecyl, n-hexadecyl, n-octadecyl, C$_{2-10}$-hydroxyalkyl, preferably C$_{2-8}$-hydroxyalkyl, particularly preferably C$_{2-4}$-hydroxyalkyl, such as 2-hydroxyethyl, 2-hydroxy-n-propyl, 3-hydroxy-n-propyl and 1-(hydroxymethyl)ethyl, particularly preferably 2-hydroxyethyl.

These 2-(hydroxyethyl)ammonium hydroxides are accessible to the person skilled in the art by known processes. In particular, they are accessible by the reaction of the corresponding tertiary amine R$^1$R$^2$R$^3$N (e.g. Et$_3$N, fatty amine, TEOA) with one mole equivalent of ethylene oxide and water.

Compare for [tetrakis(2-hydroxyethyl)ammonium] hydroxide e.g.: A. R. Doumaux et al. J. Org. Chem. 1973, 38 (20), pages 3630-3632, and DE-A-22 17 494 and DE-A-21 21 325 (both BASF AG).

One advantage of the ammonium hydroxide is that the quaternary ammonium salt dissolves completely in the triethanolamine mixture and at least partially neutralizes the H$_3$PO$_3$ and/or H$_3$PO$_2$ (buffer effect).

Particularly preferred ammonium hydroxides are [tetrakis(2-hydroxyethyl)ammonium] hydroxide and [(C$_{1-4}$-alkyl)$_3$(2-hydroxyethyl)ammonium] hydroxide, such as, for example, [triethyl(2-hydroxyethyl)ammonium] hydroxide.

A further advantage of the particularly preferred [tetrakis(2-hydroxyethyl)ammonium] hydroxide arises from the fact that, under the conditions of the triethanolamine distillation, the base decomposes partially or completely to give water and the product of value triethanolamine and therefore does not need to be separated off from the product of value. No problems resulting from salt formation arise.

A further advantage of a (2-hydroxyethyl)ammonium hydroxide based on a fatty amine ((C$_{8-30}$)$_3$N) is the fact that, under the conditions of the triethanolamine distillation, the base partially or completely decomposes to give water and the fatty amine and the fatty amine can easily be separated off from the pure TEOA via the distillation bottoms as a high-boiling component.

Preferably, the molar ratio of acid(s) used to ammonium hydroxide used is 1:1 to 100:1, particularly 1.1:1 to 10:1, in particular 1.2:1 to 8:1, very particularly 1.3:1 to 6:1.

In the case of alkali metal hydroxide as basic compound, the molar ratio of acid(s):hydroxide is preferably in the range from 1:0.2 to 1:0.9, in particular 1:0.3 to 1:0.8, very particularly 1:0.4 to 1:0.7, e.g. 1:0.5 to 1:0.6.

In the case of alkaline earth metal hydroxide as basic compound, the molar ratio of acid(s):hydroxide is preferably in the range from 1:0.1 to 1:0.45, in particular 1:0.15 to 1:0.4, very particularly 1:0.2 to 1:0.35.

If phosphorous acid and hypophosphorous acid are used together, the above molar ratio data refer to both acids together.

For example, 1000 ppm of $H_3PO_3$ and between 320 and 2573 ppm of the basic compound [tetrakis(2-hydroxyethyl) ammonium] hydroxide are added to the TEOA.

The basic compound can firstly be added to the TEOA, followed by the acid(s). In a preferred procedure, the acid(s) is/are firstly added to the TEOA and then the basic compound is added.

In another preferred procedure, a mixture of the acid(s) with the basic compound is firstly prepared and this mixture is then added to the TEOA.

In order to improve the handling properties it may be advantageous here to meter in the effective amount of phosphorous acid and/or hypophosphorous acid in a suitable inert diluent or solvent, such as, for example, water, alcohols (methanol, ethanol, isopropanol, n-propanol, n-butanol, 2-butanol), ethers (tetrahydrofuran, 1,4-dioxane) or an alkanolamine (e. g. an ethanolamine, such as monoethanolamine, diethanolamine, N-(2-aminoethyl)ethanolamine, in particular triethanolamine), in the form of a solution or a suspension.

The basic compound can advantageously be used as a solution or suspension in water, e.g. as a 30 to 80% strength by weight, in particular 40 to 60% strength by weight, solution or suspension.

[Tetrakis(2-hydroxyethyl)ammonium] hydroxide is commercially available in the form of a 50% strength by weight aqueous solution and it can be used advantageously.

The required treatment time of the triethanolamine with the addition of acid and basic compound arises inter alia from the degree of discoloration of the triethanolamine used and the extent of desired decoloration and/or color stability of the TEOA. For a given temperature the higher the degree of discoloration of the triethanolamine used in the process according to the invention and the higher the requirements placed on the color quality of the process product, the greater the time.

The temperature must, however, not be chosen to be too high, i.e. generally not higher than 250° C. since otherwise an acid-induced degradation of the triethanolamine can take place which adversely affects the color quality of the TEOA ultimately obtained. The temperatures and treatment times which are most favorable for the particular triethanolamine used are easy to ascertain in simple preliminary experiments.

During this treatment of the triethanolamine with the acid and the basic compound it is advantageous if the mixture is further mixed (e.g. stirred or circulated by pump) throughout the entire treatment time or at intervals.

It is also advantageous if the treatment of the triethanolamine is carried out under a protective gas atmosphere (e.g. $N_2$ or Ar), i.e. in the absence of $O_2$.

The treatment of the alkanolamine with the acid and the basic compound can also be carried out continuously in suitable containers, e.g. in a tubular reactor or in a cascade of stirred containers.

The treatment of the triethanolamine with the acid and the basic compound can be carried out advantageously in the bottoms container of a distillation column or in a distillation initial charge vessel before and/or during the distillation of the triethanolamine.

In a particular embodiment during the treatment of the triethanolamine with the acid and the basic compound an inert gas (e.g. $N_2$ or Ar) is passed as a stripping stream through the triethanolamine in order to remove from the mixture any low-boiling components which form and which can have an adverse effect on the color quality, such as, for example, acetaldehyde or secondary products thereof.

In another particular embodiment, the triethanolamine to be treated is circulated in liquid form via a heat exchanger and any low-boiling components which form, which can have an adverse effect on the color quality, such as, for example, acetaldehyde, are removed in the process.

The heat exchanger here may be an open heat exchanger, such as, for example, a falling-film or wiper-blade evaporator, or a sealed heat exchanger, such as, for example, a plate- or tube-bundle heat exchanger.

Depending on the reaction conditions chosen, it may be necessary to carry out the treatment of the triethanolamine with the acid and the basic compound at a superatmospheric pressure (e.g. 0.1 to 50 bar) in order to avoid the undesired escape of one or more components from the mixture.

The distillation or rectification of the triethanolamine to separate off the added compounds takes place discontinuously or continuously at a pressure of usually less than 100 mbar (100 hPa), for example at about 10 to 50 mbar or 1 to 20 mbar, preferably at 0.5 to 5 mbar, and at bottoms temperatures of generally 100 to 250° C., where in the case of the continuous procedure, in a particular embodiment, any low-boiling component fractions present are drawn off overhead and the TEOA is obtained in the side take-off.

The residue of the distillation or rectification comprising the added compounds and/or reaction products thereof can, in a particular embodiment, be completely or partially returned to the distillation process.

The method according to the invention produces a triethanolamine with improved color quality which, directly after being obtained, has a APHA color number in the range from 0 to 30, in particular from 0 to 20, very particularly from 0 to 10, e.g. 1 to 6.

All of the APHA data in this document are in accordance with DIN ISO 6271 (=Hazen). All of the ppm data in this document are based on the weight (ppm by weight).

EXAMPLES

The experiments were carried out in a laboratory apparatus consisting of a 4 liter three-necked flask with stirrer, thermometer and gas line. 1000 ppm of $H_3PO_3$ were added to a mixture of 21% by weight of diethanolamine and 79% by weight of triethanolamine and in each case varying amounts of a base, as desired.

Under reduced pressure at a bottoms temperature of about 190-195° C., diethanolamine and triethanolamine were distilled off from the flask one after the other over a period in the range from 1 to 8 h via a Vigreux column and fractions of triethanolamine with a content of at least 99.4% (GC area %) were obtained.

Color number measurements (according to Hazen) were carried out on these triethanolamine grades and documented in the table below. The yield losses as a result of secondary reactions were determined by weighing out the fractions of diethanolamine and triethanolamine (TEOA) obtained and are based on the formation of high-boiling compounds which are left behind in the bottoms following distillation.

TABLE 1

| Type, amount of additive (ppm) | Base/H$_3$PO$_3$ (molar ratio) | Content of TEOA GC area % | Color number (Hazen) | Amount of bottoms residue (% by weight) |
|---|---|---|---|---|
| H$_3$PO$_3$, 1000 | 0 | 99.6 | 5 | 5.0 |
| H$_3$PO$_3$, 1000/ Base, 320 | 1/8 | 99.5 | 2 | 2.2 |
| H$_3$PO$_3$, 1000/ Base, 645 | 1/4 | 99.7 | 5 | 4.2 |
| H$_3$PO$_3$, 1000/ Base, 1290 | 1/2 | 99.5 | 3 | 1.1 |

Base = [tetrakis(2-hydroxyethyl)ammonium]hydroxide

The additional addition of the ammonium hydroxide to the phosphorous acid brings about an increase in the distillation yield of triethanolamine without having an adverse effect on the color number, and sometimes even having a positive effect on the color number (in the sense of reducing the color number).

TABLE 2

| Type, amount of additive (ppm) | NaOH/ H$_3$PO$_3$ (molar ratio) | Content of TEOA (GC area %) | Color number (Hazen) | Amount of bottoms residue (% by weight) |
|---|---|---|---|---|
| H$_3$PO$_3$, 1000/ NaOH, 490 | 1.0 | 99.8 | 3 | 2.0 |

We claim:

1. A method comprising:
   (a) providing a composition comprising triethanolamine; and
   (b) contacting the composition with an acid component and a basic component;
   wherein the acid component comprises an acid selected from the group consisting of phosphorous acid, hypophosphorous acid and mixtures thereof; and wherein the basic component comprises a compound selected from the group consisting of alkali metal hydroxides, alkaline earth metal hydroxides, ammonium hydroxides according to general formula (I), and mixtures thereof:

[R$^1$R$^2$R$^3$(2-hydroxyethyl)ammonium] hydroxide  (I)

wherein R$^1$, R$^2$ and R$^3$ each independently represents a C$_{1-30}$ alkyl or a C$_{2-10}$ hydroxyalkyl; with the proviso that where the basic component comprises an alkali metal hydroxide, the molar ratio of acid component: basic component is 1:0.1 to 1:1, and where the basic component comprises an alkaline earth metal hydroxide, the molar ratio of acid component: basic component is 1:0.05 to 1:0.5.

2. The method according to claim 1, further comprising distilling the composition, and wherein the composition is contacted with the acid component and the basic component prior to, during or both prior to and during the distillation.

3. The method according to claim 1, wherein the composition is contacted with the acid component and the basic component for a period of at least 5 minutes.

4. The method according to claim 1, wherein the composition is contacted with the acid component and the basic component for a period of 10 minutes to 50 hours.

5. The method according to claim 1, wherein the composition is contacted with the acid component and the basic component at a temperature of 40 to 250° C.

6. The method according to claim 4, wherein the composition is contacted with the acid component and the basic component at a temperature of 40 to 250° C.

7. The method according to claim 1, wherein the acid component is present in an amount of 0.01 to 2% by weight, based on the triethanolamine.

8. The method according to claim 1, wherein the basic component comprises an ammonium hydroxide according to general formula (I), and wherein the molar ratio of acid component: basic component is 1:1 to 100:1.

9. The method according to claim 8, wherein the molar ratio of acid component: basic component is 1.1:1 to 10:1.

10. The method according to claim 1, wherein the basic component comprises an ammonium hydroxide selected from the group consisting of tetrakis (2-hydroxyethyl) ammonium hydroxide or (C$_{1-4}$-alkyl)$_3$(2-hydroxyethyl)ammonium hydroxide.

11. The method according to claim 1, wherein the basic component comprises triethyl(2-hydroxyethyl)ammonium hydroxide.

12. A composition comprising triethanolamine, an acid component and a basic component, wherein the acid component comprises an acid selected from the group consisting of phosphorous acid, hypophosphorous acid and mixtures thereof; and
wherein the basic component comprises an ammonium hydroxide according to general formula (I):

[R$^1$R$^2$R$^3$(2-hydroxyethyl)ammonium] hydroxide  (I)

wherein R$^1$, R$^2$ and R$^3$ each independently represents a C$_{1-30}$ alkyl or a C$_{2-10}$ hydroxyalkyl.

13. The composition according to claim 12, wherein the acid component is present in an amount of 0.01 to 2% by weight, based on the triethanolamine.

14. The composition according to claim 12, wherein the molar ratio of acid component: basic component is 1:1 to 100:1.

15. The composition according to claim 12, wherein the basic component comprises an ammonium hydroxide selected from the group consisting of tetrakis(2-hydroxyethyl)ammonium hydroxide or (C$_{1-4}$-alkyl)$_3$(2-hydroxyethyl)ammonium hydroxide.

16. The composition according to claim 12, wherein the basic component comprises tiethyl(2-hydroxyethyl)ammonium hydroxide.

17. A composition comprising triethanolamine, an acid component and a basic component, wherein the acid component comprises an acid selected from the group consisting of phosphorous acid, hypophosphorous acid and mixtures thereof; and
wherein the basic component comprises a compound selected from the group consisting of alkali metal hydroxides, alkaline earth metal hydroxides, and mixtures thereof; with the proviso that where the basic component comprises an alkali metal hydroxide, the molar ratio of acid component: basic component is 1:0.1 to 1:1, and where the basic component comprises an alkaline earth metal hydroxide, the molar ratio of acid component: basic component is 1:0.05 to 1:0.5.

18. The composition according to claim 17, wherein the acid component is present in an amount of 0.01 to 2% by weight, based on the triethanolamine.

19. The composition according to claim 17, wherein the basic component comprises sodium hydroxide.

20. The composition according to claim 18, wherein the basic component comprises sodium hydroxide.

* * * * *